United States Patent
Sundaram et al.

(10) Patent No.: US 7,189,853 B2
(45) Date of Patent: Mar. 13, 2007

(54) PROCESS FOR THE PREPARATION OF [R-(E)-1-[[[1-[3-[2-[7-CHLORO-2-QUINOLINYL]ETHENYL]PHENYL]-3-[2-(1-HYDROXY-1-METHYLETHYL)PHENYL]PROPYL]THIO]METHYL] CYCLOPROPANEACETIC ACID (MONTELUKAST) AND ITS PHARMACEUTICALLY ACCEPTABLE SALTS

(75) Inventors: Venkataraman Sundaram, Hyderabad (IN); Srinivasan Thirumalai Rajan, Hyderabad (IN); Veera Venkata Naga Chandra Sekhar Bulusu, Hyderabad (IN); AlokKumar Srivastav, Gorakhapur (IN); Ravi Kumar Kasturi, Hyderabad (IN); Sanjeev Kumar Aavula, Hyderabad (IN)

(73) Assignees: Dr. Reddy's Laboratories Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 49 days.

(21) Appl. No.: 10/932,562

(22) Filed: Sep. 2, 2004

(65) Prior Publication Data

US 2005/0234241 A1    Oct. 20, 2005

(30) Foreign Application Priority Data

Apr. 15, 2004   (IN) .................................. 342/04

(51) Int. Cl.
*C07D 215/18*   (2006.01)
(52) U.S. Cl. ...................................................... 546/180
(58) Field of Classification Search ................. 546/180
See application file for complete search history.

(56) References Cited

U.S. PATENT DOCUMENTS

| 5,565,473 | A | | 10/1996 | Belley et al. | |
| 5,614,632 | A | * | 3/1997 | Bhupathy et al. | ........... 546/180 |
| 5,856,322 | A | | 1/1999 | Belley et al. | |

\* cited by examiner

*Primary Examiner*—Zinna N. Davis
(74) *Attorney, Agent, or Firm*—Robert A. Franks; Edward D. Pergament; Milagros A. Cepeda

(57) ABSTRACT

The present invention is related to a process for preparing montelukast involving the compound of formula (VI):

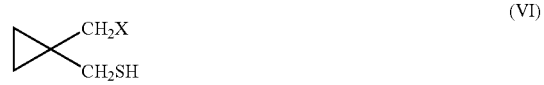

wherein X=CN or $CONH_2$.

15 Claims, No Drawings

PROCESS FOR THE PREPARATION OF [R-(E)-1-[[[1-[3-[2-[7-CHLORO-2-QUINOLINYL] ETHENYL]PHENYL]-3-[2-(1-HYDROXY-1-METHYLETHYL)PHENYL]PROPYL]THIO] METHYL]CYCLOPROPANEACETIC ACID (MONTELUKAST) AND ITS PHARMACEUTICALLY ACCEPTABLE SALTS

The present invention claims the benefit of priority of Indian Patent Application 342/CHE/2004, filed on Apr. 15, 2004, the disclosure of which are incorporated herein by reference in their entirety.

The present invention relates to a process for the preparation of [R-(E)-1-[[[1-[3-[2-[7-chloro-2-quinolinyl]ethenyl]phenyl]-3-[2-(1-hydroxy-1-methylethyl)phenyl]propyl]thio]methyl]cyclopropaneacetic acid of formula (I) (herein after referred to as Montelukast) and its pharmaceutically acceptable salts, preferably sodium salt. It may be represented as Formula (II).

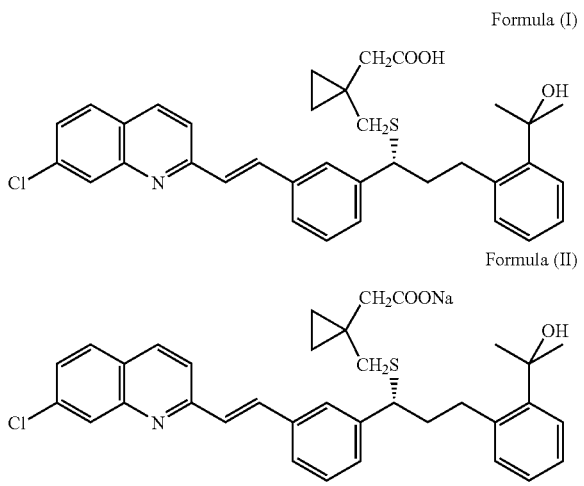

Montelukast sodium is a Leukotriene antagonist and is useful in the treatment of Asthma as well as other conditions mediated by leukotrienes, such as inflammation and allergies.

EP 480717 discloses a process for preparing montelukast sodium by reacting 2-(2-(2-(3(S)-(3-(2-(7-chloro-2-quinolinyl)-ethenyl)phenyl)-3-(methanesulfonyloxy)propyl)phenyl)-2-propoxy)tetra hydro pyran with Methyl 1-(acetylthiomethyl)cyclopropane acetate in presence of hydrazine, cesium carbonate in acetonitrile as solvent to get methyl ester of Montelukast in pyran protected form, which is further reacted with pyridinium p-toluene sulfonate, sodium hydroxide in a mixture of methanol and tetrahydrofuran as a solvent to afford Montelukast sodium of Formula (I).

In U.S. Pat. No. 5,614,632, montelukast is prepared by condensing 1-(mercaptomethyl)cyclopropaneacetic acid then condensation with 2-(2-(3(S)-(3-(2-(7-chloro-2-quinolinyl)ethenyl)phenyl)-3-methanesulfonyloxypropyl)phenyl)-2-propanol compound to afford Montelukast. It is further converted to its corresponding sodium salt via dicyclohexyl amine salt.

The prior art procedures involve more number of steps, which include a series of protections and deprotections of diol intermediate, usage of hazardous and costly raw materials such as n-butyl lithium, hydrazine, pyridinium p-toluenesulfonate in typical reaction conditions i.e., at very low temperatures (−25° C.). The processes of the prior art references involve tedious workup to isolate the required product and thus results in excess time cycle, which in turn rendering the process more costly and less eco friendly thus the process is not amenable for commercial scale up.

As Montelukast sodium of Formula (I) is a potent drug for the treatment of Asthma, it is important to have a cost effective and commercially viable novel method for preparing the compound of Formula (I).

The process for the preparation of Montelukast or its pharmaceutical salts, preferably sodium salt is cost effective and the Montelukast sodium obtained in this process is suitable for pharmaceutical formulations.

The process of the present invention utilizes the mesylation of 2-(2-(3(S)-(3-(2-(7-chloro-2-quinolinyl)ethenyl)phenyl)-3-hydroxypropyl)phenyl)-2-propanol using methane sulfonyl chloride and condensation of the resulting mesylate with a compound of formula (VI) where $X=CN$ or $CONH_2$ or mixture of compound of formula (VI) wherein $X=CN$ and compound of formula (VI) wherein $X=CONH_2$ to give a compound of formula (VII) where $X=CN$ or $CONH_2$. This compound is hydrolyzed to afford Montelukast, and it is isolated in the form of an amine salt of formula (VIII). This amine salt of Montelukast is then converted into sodium salt of Montelukast in a conventional method.

The present invention also relates to preparation of compound of formula (VI), presented by

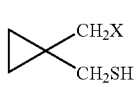

wherein $X=CN$ or $CONH_2$ or mixture of compound of formula (VI) wherein $X=CN$ and compound of formula (VI) wherein $X=CONH_2$.

The process of the present invention is schematically represented as follows.

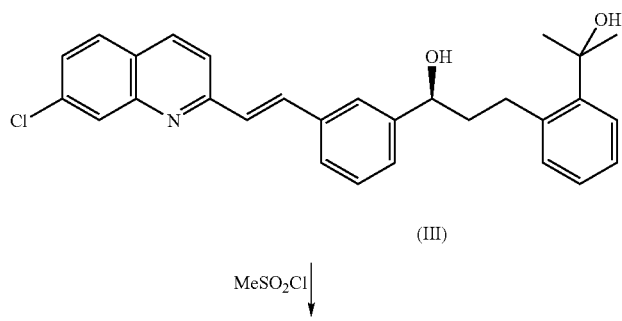

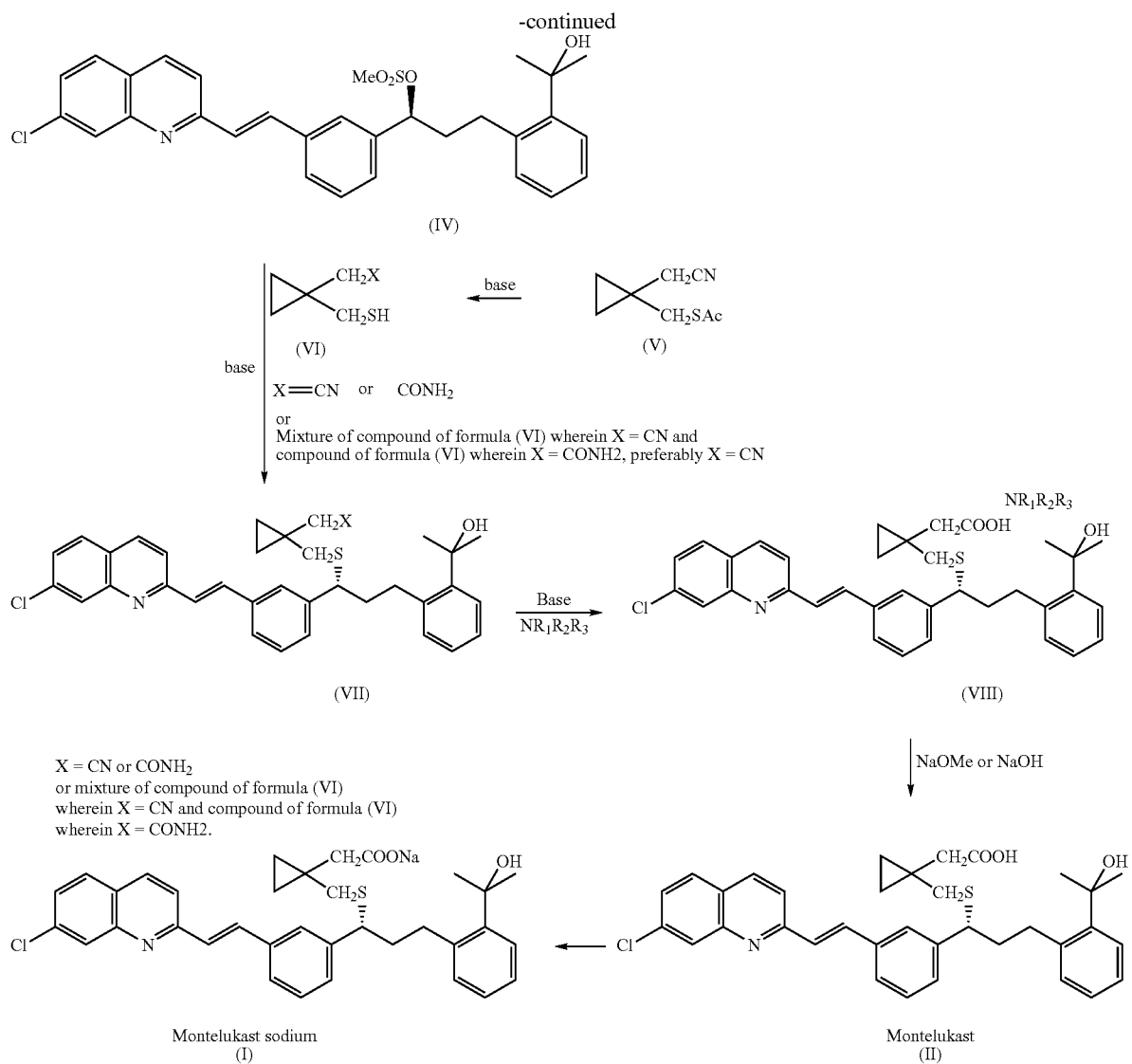

In the process, 2-(2-(3(S)-(3-(2-(7-chloro-2-quinolinyl) ethenyl)phenyl)-3-hydroxypropyl)phenyl)-2-propanol of Formula (III) is mesylated with methane sulfonyl chloride in the presence of N,N-diisopropyl ethyl amine as a base and a mixture of acetonitrile and toluene as solvent medium to yield 2-(2-(3(S)-(3-(2-(7-chloro-2-quinolinyl)ethenyl)phenyl)-3-methanesulfonyloxypropyl)phenyl)-2-propanol of Formula (IV). The compound of formula (IV) is then condensed with a compound of formula (VI), where in X=CN or $CONH_2$ or mixture of compound of formula (VI) wherein X=CN and compound of formula (VI) wherein X=$CONH_2$ and which is obtained as given in the above synthetic scheme, in a polar organic solvent in presence of a base and is isolated in the form of organic amine salt of formula (VIII). The resultant amine salt is conveniently converted into pharmaceutically acceptable salts, preferably sodium salt using sodium methoxide or sodium hydroxide.

The compound of formula (VI) can be prepared by hydrolyzing the compound of formula (V) under a basic condition, which may be prepared as per the procedure given in U.S. Pat. No. 5,614,632, incorporated herein by reference. The basic condition can be made using a base such as sodium hydroxide, sodium methoxide, sodium secondary butoxide, sodium tertiary butoxide, sodium carbonate, sodium bicarbonate, potassium hydroxide, potassium tertiary butoxide, potassium carbonate in a solvent like water, methanol, ethanol, 1-propanol, 2-propanol, 1-butanol, 2-butanol, t-butyl alcohol, glycol, diethyl ether, diisopropyl ether, methyl isopropyl ether, tetrahydrofuran, diethyl glycol, 1,4-dioxan, methoxy ethanol, toluene, cyclohexane, hexanes, n-heptane or mixtures there of.

The condensation of the compound of formula (VI) with the compound of formula (IV) can be done by dissolving the compound of formula (VI) in a solvent such as toluene, xylenes, cyclohexane, hexanes, ethyl benzene, tetrahydrofuran, N,N-dimethyl formamide, dimethyl sulfoxide, preferably N,N-dimethyl formamide or dimethyl sulfoxide; cooling the resulting solution to below 0° C.; slowly adding a base such as lithium hydroxide, lithium carbonate, n-butylithium, sodium hydroxide, sodium methoxide, sodium secondary butoxide, sodium tertiary butoxide, sodium carbonate, potassium hydroxide, potassium tertiary butoxide, potassium carbonate preferably lithium hydroxide or n-butyllithium; maintaining the temperature below 0° C. for about 20 minutes; adding 2-(2-(3(S)-(3-(2-(7-chloro-2-quinolinyl)ethenyl)phenyl)-3-sulfonyloxypropyl)phenyl)-2-propanol of formula (IV) to the alkali salt of compound of formula (VI); stirring the resulting reaction mass so obtained in step (c) below 0° C. until the reaction is substantially completed and subsequent working up using a conventional method to get a compound of formula (VII).

The hydrolysis of the compound of formula (VII) is done by using a base such as sodium hydroxide, sodium methoxide, sodium carbonate, sodium bicarbonate, potassium hydroxide, potassium carbonate, or potassium bicarbonate optionally in a alcoholic solvent like methanol, ethanol, 1-propanol, 2-propanol, 1-butanol, 2-butanol, t-butyl alcohol, glycol; a ethereal solvent like diethyl ether, diisopropyl ether, methyl isopropyl ether, tetrahydrofuran, diethylene glycol, 1,4-dioxan, methoxy ethanol; or a hydrocarbon solvent like toluene, cyclohexane, hexanes, n-heptane or mixtures there of.

Montelukast may be converted in to an amine salt using the amine $NR_1R_2R_3$, where in $R_1=R_2=R_3=H$ or $C_{1-5}$ alkyl, $C_{1-4}$ alkyl, preferably $R_1=(CH_3)_3C-$ and $R_2=R_3=H$, in a solvent such as hexanes, cyclohexane, n-heptane, methanol, ethanol, 1-propanol, 2-propanol, 1-butanol, 2-butanol, t-butyl alcohol, glycol, acetonitrile, ethyl acetate, toluene, acetone, diethyl ether, diisopropyl ether, methyl isopropyl ether, 1,4-dioxan, methoxy ethanol, diethylene glycol or mixtures there of to get [R-(E)-1-[[[1-[3-[2-[7-chloro-2-quinolinyl]ethenyl]phenyl]-3-[2-(1-hydroxy-1-methylethyl)phenyl]propyl]thio]methyl]cyclopropaneacetic acid t-butyl amine salt of formula (VIII). Then, the amine salt can be converted to Montelukast sodium by treatment with an organic acid such as formic acid, acetic acid, propanoic acid, butyric acid and by subsequent treatment with a source of sodium such as sodium methoxide, sodium hydroxide, sodium secondary butoxide or sodium tertiary butoxide, preferably sodium hydroxide or sodium methoxide in a alcoholic solvent such as methanol, ethanol, propanol, butanol, 2-propanol or tertiary butanol; or other solvent like from chloroform, dichloromethane, toluene, ethylacetate, butyl acetate, methyl isobutyl ketone, xylenes, cyclohexanes, hexanes, n-heptane, cyclopentane to get Montelukast sodium, which is substantially pure.

The Montelukast sodium obtained in the present process is free flowing and non-solvated solid. Hence, it is well suited for pharmaceutical applications. The process of the present invention is cost effective, eco-friendly and amenable for scale up.

The following Examples are provided for the purpose of giving the man of the art a sufficiently clear and complete explanation of the present invention, but must not be deemed to be limitations on the essential aspects of the object of the invention, such as those indicated in the foregoing paragraphs hereof.

EXAMPLE-1

PREPARATION OF [R-(E)-1-[[[1-[3-[2-[7-CHLORO-2-QUINOLINYL]ETHENYL]PHENYL]-3-[2-(1-HYDROXY-1-METHYL ETHYL) PHENYL]PROPYL]THIO]METHYL] CYCLOPROPANE ACETONITRILE 10 g of 2-(2-(3(S)-(3-(2-(7-chloro-2-quinolinyl)ethenyl) phenyl)-3-hydroxypropyl)phenyl)-2-propanol was added in 50 ml of toluene, and the mixture was heated to reflux. Water was removed by azeotropic distillation followed by distillation of toluene to a minimum quantity. The resulting mass was allowed to cool to ambient temperature. 90 ml of acetonitrile was added to cooled reaction mass and was stirred at 50–60° C. for 30–45 minutes. Resulting mass was further cooled to −10 to −15° C. and 5.33 ml of N,N-diisopropyl ethylamine was added and was stirred for about 30 minutes. 9.3 ml of methane sulfonyl chloride was added and seeded with 2-(2-(3(S)-(3-(2-(7-chloro-2-quinolinyl) ethenyl)phenyl)-3-methanesulphonyloxy propyl)phenyl)-2-propanol and reaction mass was aged at −10 to −15° C. for about 8–9 hours. The reaction mass was filtered and washed with acetonitrile followed by hexanes to get 10.0 g of 2-(2-(3(S)-(3-(2-(7-chloro-2-quinolinyl)ethenyl)phenyl)-3-methanesulphonyloxy propyl)phenyl)-2-propanol.

32.3 g of 1-(Mercaptomethyl)cyclopropane was dissolved acetonitrile in 400 ml of N,N-dimethylformamide and the mixture was cooled to −10 to −15° C. 317.5 ml of 3.4 M n-Butyl lithium was added drop wise in reaction mass. 80 g of above obtained 2-(2-(3(S)-(3-(2-(7-chloro-2-quinolinyl) ethenyl)phenyl)-3-methanesulphonyloxypropyl)phenyl)-2-propanol was added to the reaction mass at −10 to −15° C. and the reaction mass was aged at −10 to −15° C. for about 6–8 hours. Then added 500 ml of 15% sodium chloride solution followed by 800 ml of toluene and stirred the reaction mass for about 20 minutes. Organic layer and aqueous layer were separated. Aqueoues layer was extracted with toluene. Water was added to combine organic layer and pH was adjusted to 5–5.5 using 48 ml of acetic acid and reaction mass was stirred at 25–35° C. for 30–40 minutes. Organic layer was washed with 640 ml of 5% Sodium bicarbonate solution followed by water 8 gm of carbon and sodium sulfate were added to the organic layer and stirred for 15–30 minutes, was filtered and washed with toluene followed by removal of solvent under vaccum below 50° C. to afford 80 g of [R-(E)-1-[[[1-[3-[2-[7-chloro-2-quinolinyl] ethenyl]phenyl]-3-[2-(1-hydroxy-1-methylethyl)phenyl] propyl]thio]methyl]cyclopropane acetonitrile.

EXAMPLE-2

PREPARATION OF [R-(E)-1-[[[1-[3-[2-[7-CHLORO-2-QUINOLINYL]ETHENYL]PHENYL]-3-[2-(1-HYDROXY-1-METHYL ETHYL) PHENYL]PROPYL]THIO]METHYL] CYCLOPROPANE ACETICACID, T-BUTYLAMINE SALT

Method A:

6.5 g of R-(E)-1-[[[1-[3-[2-[7-chloro-2-quinolinyl]ethenyl]phenyl]-3-[2-(1-hydroxy-1-methylethyl)phenyl]propyl] thio]methyl]cyclopropane acetonitrile and 325 ml of caustic lye was added into round bottom flask and further stirred and heated to reflux at 118–122° C. for 6 to 8 hours. 130 ml of water, 650 ml of toluene was added to the reaction mass below 90° C. and stirred for 20–30 minutes. Organic and aqueous layer were separated and aqueous layer was extracted with 325 ml of toluene at 60–70° C. Combined organic layer was distilled under vaccum below 50° C. and washed with 720 ml of n-heptane at 25–35° C. 300 ml of water and 200 ml of dichloromethane were added to the reaction mass and stirred. pH of reaction mass was adjusted to 4.8 to 5 with acetic acid. Organic and aqueous layer were separated and aqueous layer was extracted with 200 ml of dichloromethane. Combined total organic layer was washed with 1300 ml of water and distilled off solvent from organic layer at atomspheric pressure followed by vaccum below 50° C. to afford [R-(E)-1-[[[1-[3-[2-[7-chloro-2-quinolinyl]

ethenyl]phenyl]-3-[2-(1-hydroxy-1-methylethyl)phenyl]propyl]thio]methyl]cyclopropane acetic acid 0.212 ml of acetone was added to the above obtained crude and distilled of acetone under vaccum below 50° C. to remove the traces of dichloromethane. 21 gm of tertiary butyl amine was added to the above reaction mass slowly at 25–30° C. and seeded. The reaction mass was stirred for thick solid separation at 25–35° C. for 8–10 hours. The separated solid was filtered and washed with acetone. It was then dried at 50–55° C. to afford 40 gm of R-(E)-1-[[[1-[3-[2-[7-chloro-2-quinolinyl]ethenyl]phenyl]-3-[2-(1-hydroxy-1-methyl ethyl)phenyl]propyl]thio]methyl]cyclopropane acetic acid, t-butylamine salt.

The above compound was purified by dissolving 30 gm of R-(E)-1-[[[1-[3-[2-[7-chloro-2-quinolinyl]ethenyl]phenyl]-3-[2-(1-hydroxy-1-methyl ethyl)phenyl]propyl]thio]methyl]cyclopropane acetic acid, t-butylamine salt in 360 ml of acetone and heated to reflux for 1 to 2 hours. It was then cooled to 25–35° C. and maintained at 25–35° C. for 6–8-hours. The resultant solid was filtered and washed with acetone. The solid was dried at 50–55° C. to afford 23.8 gm of pure R-(E)-1-[[[1-[3-[2-[7-chloro-2-quinolinyl]ethenyl]phenyl]-3-[2-(1-hydroxy-1-methyl ethyl)phenyl]propyl]thio]methyl]cyclopropane acetic acid, t-butylamine salt.

Method B:

13.5 g of R-(E)-1-[[[1-[3-[2-[7-chloro-2-quinolinyl]ethenyl]phenyl]-3-[2-(1-hydroxy-1-methylethyl)phenyl]propyl]thio]methyl]cyclopropane acetonitrile, 94.5 ml of Diethyleneglycol and solution of 10.7 g potassium hydroxide in 40 ml of water were added in round bottom flask and the mixture was refluxed for 24 hours. The reaction mass was cooled to ambient temperature and washed with 325 ml of toluene. 54 ml of water was added to the reaction mass and the product was extracted with 472.5 ml of ethyl acetate. Organic layer was washed with aqueous acetic acid followed by 50 ml of 5% of sodium bicarbonate solution. The solvent was evaporated from the organic layer to afford 7.5 g of [R-(E)-1-[[[1-[3-[2-[7-chloro-2-quinolinyl]ethenyl]phenyl]-3-[2-(1-hydroxy-1-methylethyl)phenyl]propyl]thio]methyl]cyclopropane acetic acid. Above obtained compound was added into 45 ml of acetone. 1.5 ml of t-butylamine was added to reaction mass and stirred for about 20 hours. The separated solid was filtered and washed with acetone followed by hexanes to get 4.3 g of R-(E)-1-[[[1-[3-[2-[7-chloro-2-quinolinyl]ethenyl]phenyl]-3-[2-(1-hydroxy-1-methyl ethyl)phenyl]propyl]thio]methyl]cyclopropane aceticacid, t-butylamine salt.

The above compound was purified by recrystallization from solvents like ethyl acetate, a mixture of isopropyl alcohol and acetonitrile or a mixture of methanol and acetonitrile.

EXAMPLE-3

PREPARATION OF [R-(E)-1-[[[1-[3-[2-[7-CHLORO-2-QUINOLINYL]ETHENYL]PHENYL]-3-[2-(1-HYDROXY-1-METHYL ETHYL)PHENYL]PROPYL]THIO]METHYL]CYCLOPROPANE ACETICACID, MONOSODIUM SALT 20.0 g of [R]-1-[[[1-[3-[2-(7-chloro-2-quinolinyl)ethenyl]phenyl]-3-[2-(1-hydroxy-1-methyl ethyl)-phenyl]propyl]thio]methyl]cyclopropane acetic acid, tertiary butyl amine salt (Montelukast tertiary butyl amine salt) and dichloromethane (50 ml) was added into round bottom flask at 25–35° C. Acetic acid (2.62 ml) and water (100 ml) were added to the reaction mass, was stirred at 25–35° C. for 30–60 minutes. The organic layer and aqueous layer were separated. Aqueous layer was extracted with dichloromethane (40 ml). Organic layer was washed with water (4×25 ml) and dried over sodium sulphate and filtered and washed with 20 ml of dichloromethane below 50° C. Distilled off solvent completely from organic layer under reduced pressure below 50° C. Residual mass was dissolved in methanol (200 ml) and distilled off solvent completely under reduced pressure below 50° C. Residual mass was dissolved in 100 ml of methanol. Freshly prepared solution of sodium hydroxide (1.21 grams) pellets in methanol (100 ml) was added to the residual mass at 25–35° C. under nitrogen atm and stirred for 30–60 minutes at 25–35° C. carbon (0.5 grams) was added to reaction mass and stirred for 30 minutes at 25–35° C. Filtered the carbon and washed with methanol. Distilled off solvent completely under reduced pressure below 50° C. The obtained crude was dissolved in toluene (40 ml) and distilled off solvent completely under reduced pressure below 50° C. Finally crude was dissolved in toluene (30 ml) and added to 200 ml of n-heptane under nitrogen atmosphere at 25–35° C. Maintained the reaction mass at 25–35° C. for 1 to 2 hours. The compound was filtered and washed with n-heptane (40 ml) under nitrogen atmosphere and dried at 70–75° C. for 4–5 hours to afford 16.8 grams of amorphous title compound with moisture contain less than 2%.

EXAMPLE-4

PREPARATION OF MIXTURE OF [R-(E)-1-[[[1-[3-[2-[7-CHLORO-2-QUINOLINYL]ETHENYL]PHENYL]-3-[2-(1-HYDROXY-1-METHYLETHYL)PHENYL]PROPYL]THIO]METHYL]CYCLOPROPANE ACETAMIDE AND [R-(E)-1-[[[1-[3-[2-[7-CHLORO-2-QUINOLINYL]ETHENYL]PHENYL]-3-[2-(1-HYDROXY-1-METHYLETHYL)PHENYL]PROPYL]THIO]METHYL]CYCLOPROPANE ACETONITRILE

Taken 240 mg of about 3:2 mixture of 1-(Mercaptomethyl)cyclopropane acetamide and 1-(Mercaptomethyl)cyclopropane acetonitrile in 20 ml of N,N-dimethylformamide and the mixture is cooled to below 0° C. and added 1 ml of 1.6 M n-Butyl lithium in hexanes drop wise and stirred for about 20 minutes. 450 mg of 2-(2-(3(S)-(3-(2-(7-chloro-2-quinolinyl)ethenyl)phenyl)-3-methanesulphonyloxypropyl)phenyl)-2-propanol prepared as in example-1, below 0° C. and the reaction mass is aged below 0° C. for about 5 hours. After subsequent work up as in example-1 afforded 400 mg of about 3:2 mixture of [R-(E)-1-[[[1-[3-[2-[7-chloro-2-quinolinyl]ethenyl]phenyl]-3-[2-(1-hydroxy-1-methylethyl)phenyl]propyl]thio]methyl]cyclopropane acetamide and [R-(E)-1-[[[1-[3-[2-[7-chloro-2-quinolinyl]ethenyl]phenyl]-3-[2-(1-hydroxy-1-methylethyl)phenyl]propyl]thio]methyl]cyclopropane acetonitrile.

EXAMPLE-5

PREPARATION OF R-(E)-1-[[[1-[3-[2-[7-CHLORO-2-QUINOLINYL]ETHENYL]PHENYL]-3-[2-(1-HYDROXY-1-METHYL ETHYL)PHENYL]PROPYL]THIO]METHYL]CYCLOPROPANE ACETICACID

The mixture of [R-(E)-1-[[[1-[3-[2-[7-chloro-2-quinolinyl]ethenyl]phenyl]-3-[2-(1-hydroxy-1-methylethyl)phenyl]propyl]thio]methyl]cyclopropane acetamide and [R-(E)-1-[[[1-[3-[2-[7-chloro-2-quinolinyl]ethenyl]phenyl]-3-[2-(1-hydroxy-1-methylethyl)phenyl]propyl]thio]methyl] cyclopropane acetonitrile obtained from example-4 is hydrolyzed by following the procedure of example-2 to afford R-(E)-1-[[[1-[3-[2-[7-chloro-2-quinolinyl]ethenyl]phenyl]-3-[2-(1-hydroxy-1-methyl ethyl)phenyl]propyl]thio]methyl]cyclopropane aceticacid.

EXAMPLE-6

PREPARATION OF 1-(MERCAPTOMETHYL)CYCLOPROPANE ACETONITRILE 51.0 g of 1-(Acetylthiomethyl)cyclopropane acetonitrile (prepared as per the procedure disclosed in U.S. Pat. No. 5,614,632) was dissolved in 24.4 gm of methanol and it was allowed to cool to −15 to −12° C. 24.4 g of sodium methoxide was dissolved in 127.5 ml of methanol and transferred this solution to above reaction mass at −15 to −12° C. and stirred at −15 to −12° C. 484.5 ml of water was added to the reaction mass under stirring below 0° C. and washed with 1020 ml of heptane. Aqueous layer was acidified with 65.3 ml of acetic acid and stirred the reaction mixture below 0° C. for 20–30 minutes. The organic and aqueous layer was separated. Aqueous layer was extracted with 204 ml of dichloromethane and combine organic layer was washed with 5% of 102 ml of sodium bicarbonate followed by 459 ml of water. 5.1 gm of carbon and sodium sulphate were added to combine organic layer and stirred for 15.30 minutes. Reaction mass was filtered over hyflowbed and washed with 51 ml of dichloromethane followed by removal of solvent completely from organic layer by vaccum distillation below 50° C. to afford 27.0 g of 1-(Mercaptomethyl)cyclopropane acetonitrile.

EXAMPLE-7

PREPARATION OF MIXTURE OF 1-(MERCAPTOMETHYL)CYCLOPROPANE ACETAMIDE AND 1-(MERCAPTOMETHYL)CYCLOPROPANE ACETONITRILE MIXTURE OF 1-(MERCAPTOMETHYL)CYCLOPROPANE ACETAMIDE AND 1-(MERCAPTOMETHYL) CYCLOPROPANE ACETONITRILE 2.5 g of 1-(Acetylthiomethyl)cyclopropane acetonitrile (prepared as per the procedure disclosed in U.S. Pat. No. 5,614,632) was dissolved in 25 ml of methanol and stirred at ambient temperature. 2.5 g of potassium hydroxide was dissolved in 10.0 ml of water and transferred this solution to above reaction mass. The reaction mass was then aged below 50° C. temperature until reaction is substantially completes. Then 40 ml of water was added to reaction mass and washed with 120 ml of hexanes. Aqueous phase was extracted with 160 ml of ethyl acetate. Organic layer was then washed with aqueous acetic acid followed by 5% of sodium bicarbonate solution and then washed with water. Evaporate the solvent from the organic layer to afford 600 mg of about 3:2 mixture of 1-(Mercaptomethyl)cyclopropane acetamide and 1-(Mercaptomethyl)cyclopropane acetonitrile.

What is claimed is:

1. A process for the preparation of [R-(E)-1-[[[1-[3-[2-[7-chloro-2-quinolinyl] ethenyl] phenyl]-3-[2-(1-hydroxy-1-methylethyl) phenyl] propyl] thio]methyl] cyclopropaneacetic acid, which comprises:
   (a) reacting 2-(2-(3(S)-(3-(2-(7-chloro-2-quinolinyl) ethenyl) phenyl)-3-sulfonyl oxy propyl) phenyl)-2-propanol of formula (IV) with an alkali salt of the compound of formula (VI),

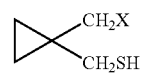

(VI)

wherein X=CN or CONH$_2$ or a mixture thereof in a solvent to get the compound of formula (VII)

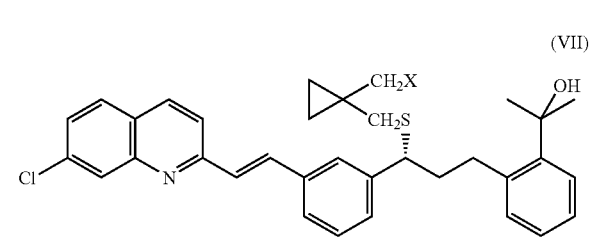

(VII)

wherein X=CN or CONH$_2$ or a mixture thereof; and
   (b) hydrolyzing the compound of formula (VII) obtained from step (a) to Montelukast in the presence of a base selected from sodium hydroxide, sodium methoxide, sodium secondary butoxide, sodium tertiary butoxide, sodium carbonate, sodium bicarbonate, potassium hydroxide, potassium tertiary butoxide, and potassium carbonate optionally in the solvent selected from the group consisting of methanol, ethanol, 1-propanol, 2-propanol, 1-butanol, 2-butanol, t-butyl alcohol, glycol; diethyl ether, diisopropyl ether, methyl isopropyl ether, tetrahydrofuran, diethylene glycol, 1,4-dioxan, methoxy ethanol; and toluene, cyclohexane, hexanes, n-heptane and mixtures of two or more miscible solvents thereof, to get montelukast.

2. The process according to claim 1, wherein the alkali salt of compound of formula (VI)

(VI)

wherein X=CN or CONH$_2$ or a mixture thereof, is a lithium salt.

3. The process according to claim 1 wherein the solvent of step (a) is selected from toluene, xylenes, cyclohexane, hexanes, ethyl benzene, tetrahydrofuran, N,N-dimethyl formamide, and dimethyl sulfoxide.

4. The process according to claim 1 wherein the solvent of step (a) is N,N-dimethyl formamide or dimethyl sulfoxide.

5. The process according to claim 1 wherein the base of step (b) is sodium hydroxide.

6. A process for preparing montelukast or a salt thereof, comprising reacting 2-(2-(3(S)-(3-(2-(7-chloro-2-quinolinyl)ethenyl)phenyl)-3-sulfonyl oxy propyl)phenyl)-2-propanol with a compound having the formula

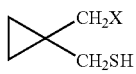

wherein X is ON, in the presence of a base to form a compound having the formula

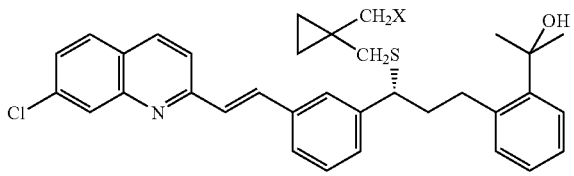

wherein X is ON.

7. The process of claim 6, wherein a base comprises lithium hydroxide or n-butyl lithium.

8. The process of claim 6, wherein a compound having the formula

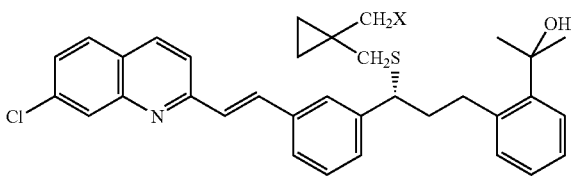

is hydrolyzed with a base to form montelukast.

9. The process of claim 8, wherein montelukast is reacted with an amine to form an amine salt, and an amine salt is sequentially treated with an organic acid and a sodium compound to form montelukast sodium.

10. The process of claim 9, wherein an amine comprises t-butyl amine.

11. A process for preparing montelukast or a salt thereof, comprising reacting 2-(2-(3(S)-(3-(2-(7-chloro-2-quinoli-nyl)ethenyl)phenyl)-3-sulfonyl oxy propyl)phenyl)-2-propanol with a compound having the formula

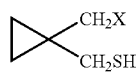

wherein X is $CONH_2$, in the presence of a base to form a compound having the formula

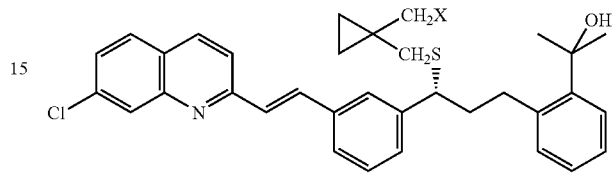

wherein X is $CONH_2$.

12. The process of claim 11, wherein a base comprises lithium hydroxide or n-butyl lithium.

13. The process of claim 11, wherein a compound having the formula

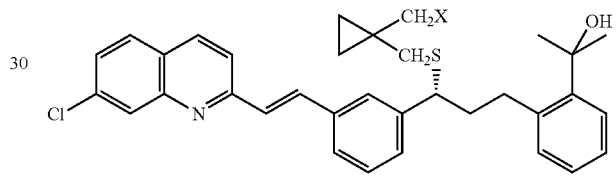

is hydrolyzed with a base to form montelukast.

14. The process of claim 13, wherein montelukast is reacted with an amine to form an amine salt, and an amine salt is sequentially treated with an organic acid and a sodium compound to form montelukast sodium.

15. The process of claim 14, wherein an amine comprises t-butyl amine.

* * * * *